(12) United States Patent
Nakazato et al.

(10) Patent No.: US 6,392,086 B1
(45) Date of Patent: May 21, 2002

(54) INTERMEDIATES AND PROCESS FOR PRODUCING FLUORINE-CONTAINING AMINO ACID COMPOUND BY USING THE SAME

(75) Inventors: Atsuro Nakazato; Toshihito Kumagai; Kazunari Sakagami; Kazuyuki Tomisawa; Hisanako Ito; Takeo Taguchi, all of Tokyo (JP)

(73) Assignee: Taisho Pharmaceutical Co., Ltd. (JP)

( * ) Notice: Subject to any disclaimer, the term of this patent is extended or adjusted under 35 U.S.C. 154(b) by 0 days.

(21) Appl. No.: 09/857,631

(22) PCT Filed: Dec. 17, 1999

(86) PCT No.: PCT/JP99/07096

§ 371 Date: Jun. 7, 2001

§ 102(e) Date: Jun. 7, 2001

(87) PCT Pub. No.: WO00/37410

PCT Pub. Date: Jun. 29, 2000

(30) Foreign Application Priority Data

Dec. 18, 1998 (JP) ............................. 10-361701

(51) Int. Cl.$^7$ ............................................... C07C 69/74
(52) U.S. Cl. ........................ 560/119; 560/114; 560/118; 560/125; 560/128; 562/400; 562/498; 562/500; 562/501; 562/510; 564/123
(58) Field of Search .......................... 560/119; 562/114, 562/125, 128, 400, 498, 500, 501, 510; 564/123

(56) References Cited

U.S. PATENT DOCUMENTS 5,958,960 A 9/1999 Massey et al. ............... 514/393

FOREIGN PATENT DOCUMENTS

| EP | 0 878 463 A1 | 5/1998 |
| EP | 1 052 246 A1 | 1/1999 |
| JP | 11-279129 | 12/1999 |
| WO | 98/51655 | 5/1998 |
| WO | 99/28839 | 1/1999 |
| WO | 99/38839 | 1/1999 |
| WO | WO 2000037410 | * 6/2000 |

OTHER PUBLICATIONS

Nakazato et al, Journal of Medicinal Chemistry, 2000, 43 (25) pp4893–4909.*
Preliminary International Search Report, PCT JP/07096.*
Tetrahedron Letters 39 (1998) 9305–9308, Dominguez et al.

* cited by examiner

Primary Examiner—Paul J. Killos
Assistant Examiner—Hector M Reyes
(74) Attorney, Agent, or Firm—Lorusso & Loud

(57) ABSTRACT

The present inventions relate to a (1S,5R,6S)- or (1SR, 5RS, 6SR)-3-fluoro-2-oxobicyclo[3.1.0]hex-3-ene-6-carboxylic acid derivative represented by Formula (1):

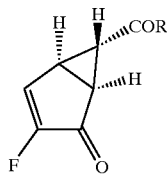

(1)

[in the formula, R represents OR$^1$ or NR$^1$R$^2$, wherein R$^1$ and R$^2$ are identical or different, and each represents a hydrogen atom, a C$_1$–C$_6$ alkyl group, a C$_3$–C$_6$ cycloalkyl group, a (C$_3$–C$_6$ cycloalkyl) (C$_1$–C$_6$ alkyl) group, an aryl group, an aryl (C$_1$–C$_6$ alkyl) group, a (C$_1$–C$_6$ alkoxy) (C$_1$–C$_6$ alkyl) group, a C$_1$–C$_6$ hydroxyalkyl group, a (C$_1$–C$_6$ alkylthio) (C$_1$–C$_6$ alkyl) group, or a C$_1$–C$_6$ mercaptoalkyl group], and a process for producing the same, and a process for efficiently producing a fluorine-containing amino acid compound acting on group 2 metabotropic glutamate receptors, which has treatment effects or prevention effects on psychiatric diseases or neurological diseases, characterized by hydrogenating the derivative, and subsequently, subjecting it to hydantoination or aminocyanidation, followed by hydrolysis.

6 Claims, No Drawings

INTERMEDIATES AND PROCESS FOR PRODUCING FLUORINE-CONTAINING AMINO ACID COMPOUND BY USING THE SAME

FIELD OF TECHNOLOGY

The present invention relates to 3-fluoro-2-oxobicyclo[3.1.0]hex-3-ene-6-carboxylic acid derivatives and a process for producing the same, and a process for producing a fluorine-containing amino acid derivative (2-amino-3-fluorobicyclo[3.1.0]hexane-2,6-dicarboxylic acid).

BACKGROUND ART

In recent years, with the repeated cloning of glutamate receptor genes, it has become clear that there are surprisingly many subtypes of glutamate receptors. At present, glutamate receptors are roughly classified into two types: the "ionotropic type", in which the receptor has an ion channel type structure, and the "metabotropic type", in which the receptor is coupled to G-proteins. Ionotropic receptors are classified pharmacologically into three types: N-methyl-D-aspartic acid (NMDA), α-amino-3-hydroxy-5-methylisoxazole-4-propionate (AMPA), and kainate (Science, 258, 597–603, 1992). Metabotropic receptors are classified into eight types, type 1 through type 8 (J. Neurosci., 13, 1372–1378, 1993; Neuropharmacol., 34, 1–26, 1995).

The metabotropic glutamate receptors are classified pharmacologically into three groups. Of these, group 2 (mGluR2/mGluR3) bind with adenylcyclase, and inhibit the accumulation of the Forskolin stimulation of cyclic adenosine monophosphate (cAMP) (Trends Pharmacol. Sci., 14, 13 (1993)), and for this reason, it is suggested that the compounds acting on group 2 metabotropic glutamate receptors have treatment effects and prevention effects on psychiatric disorders such as, for example, schizophrenia, anxiety and its associated diseases, depression, bipolar disorder and epilepsy; and neurological diseases such as drug dependence, cognitive disorders, Alzheimer's disease, Huntington's chorea, Parkinson's disease, dyskinesia associated with muscular stiffness, cerebral ischemia, cerebral failure, myelopathy, and head trauma.

In addition, in PCT/JP99/00324 which is the International Patent Application by the present applicant, 2-amino-3-fluorobicyclo[3.1.0]hexane-2,6-dicarboxylic acid as a compound acting on group 2 metabotropic glutamate receptors is disclosed. Furthermore, in the specification of the same, a preparation method thereof as described below, which comprises steps of subjecting an (1S, 5R, 6S)- or (1SR, 5RS, 6SR)-2-oxobicyclo[3.1.0]hexane-6-carboxylic acid derivative (8) to fluorination, and then, hydantoination, followed by hydrolysis, is proposed.

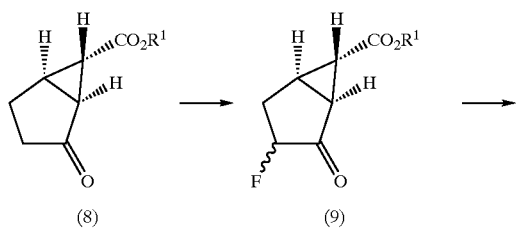

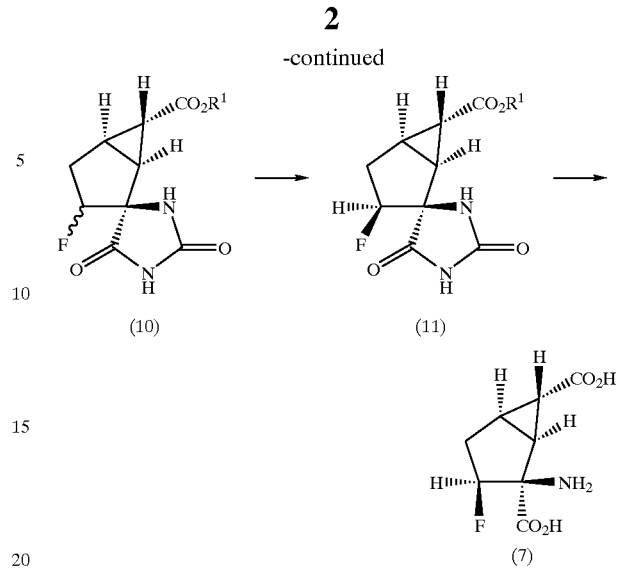

Heretofore, no synthesis methods of 2-amino-3-fluorobicyclo[3.1.0]hexane-2,6-dicarboxylic acid, other than that of the synthesis schemes described above, have been reported.

DISCLOSURE OF THE INVENTION

An object of the present invention is to provide a process for further efficiently producing a fluorine-containing amino acid derivative (2-amino-3-fluorobicyclo[3.1.0]hexane-2,6-dicarboxylic acid) acting on group 2 metabotropic glutamate receptors, which has treatment effects and prevention effects on psychiatric disorders such as schizophrenia, anxiety and its associated diseases, depression, bipolar disorder, and epilepsy, and neurological diseases such as drug dependence, cognitive disorders, Alzheimer's disease, Huntington's chorea, Parkinson's disease, dyskinesia associated with muscular stiffness, cerebral ischemia, cerebral failure, myelopathy, and head trauma, as well as novel intermediates which are useful for said production process, and a process for producing the intermediates.

After conducting diligent research with regard to a process for producing a fluorine-containing amino acid derivative [(1S, 2S, 3S, 5R, 6S)- or (1SR, 2SR, 3SR, 5RS, 6SR)-2-amino-3-fluorobicyclo[3.1.0]hexane-2,6-dicarboxylic acid], the present inventors discovered a process for efficiently producing the same, which to employ an (1S, 5R, 6S)- or (1SR, 5RS, 6SR)-2-oxobicyclo[3.1.0]hex-3-ene-6-carboxylic acid derivative as a starting material, via an (1S, 5R, 6S)- or (1SR, 5RS, 6SR)-3-fluoro-2-oxobicyclo[3.1.0]hex-3-ene-6-carboxylic acid derivative which is a novel intermediate, consequently completed the present invention.

That is, the present invention corresponds to a 3-fluoro-2-oxobicyclo[3.1.0]hex-3-ene-6-carboxylic acid derivative represented by Formula (1):

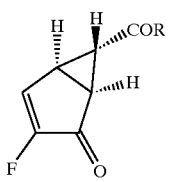

(1)

[in the formula, R represents $OR^1$ or $NR^1R^2$, wherein $R^1$ and $R^2$ are identical or different, and each represents a hydrogen atom, a $C_1$–$C_6$ alkyl group, a $C_3$–$C_6$ cycloalkyl group, a ($C_3$–$C_6$ cycloalkyl) ($C_1$–$C_6$ alkyl) group, an aryl group, an aryl ($C_1$–$C_6$ alkyl) group, a ($C_1$–$C_6$ alkoxy) ($C_1$–$C_6$ alkyl) group, a $C_1$–$C_6$ hydroxyalkyl group, a ($C_1$–$C_6$ alkylthio) ($C_1$–$C_6$ alkyl) group, or a $C_1$–$C_6$ mercaptoalkyl group], and a process for producing the derivative of Formula (1), characterized in that the process comprises the steps of:

oxidizing an (1S, 5R, 6S)- or (1SR, 5RS, 6SR)-2-oxobicyclo[3.1.0]hex-3-ene-6-carboxylic acid derivative represented by Formula (2):

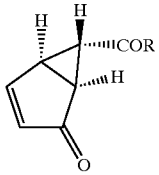

(2)

[in the formula, R is the same as described above] by means of a peroxide, to produce an (1S, 3R, 4R, 5R, 6S)- or (1SR, 3RS, 4RS, 5RS, 6SR)-epoxy derivative represented by Formula (3):

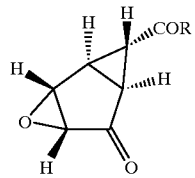

(3)

[in the formula, R is the same as described above]; and reacting said epoxy derivative with a fluorination agent, and a process for producing (1S, 2S, 3S, 5R, 6S)- or (1SR, 2SR, 3SR, 5RS, 6SR)-2-amino-3-fluorobicyclo[3.1.0]hexane-2,6-dicarboxylic acid represented by Formula (7):

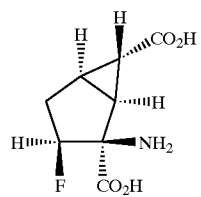

(7)

a pharmaceutically acceptable salt thereof, or a hydrate thereof, characterized in that the process comprises the steps of:

hydrogenating the derivative represented by Formula (1), to produce an (1S, 3S, 5R, 6S)- or (1SR, 3SR, 5RS, 6SR)-3-fluoro-2-oxobicyclo[3.1.0]hexane-6-carboxylic acid derivative represented by Formula (4):

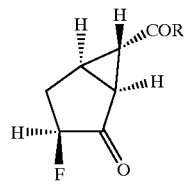

(4)

[in the formula, R is the same as described above]; subjecting the same to hydantoination or aminocyanidation, to produce an (1S, 2S, 3S, 5R, 6S)- or (1SR, 2SR, 3SR, 5RS, 6SR)-hydantoin derivative represented by Formula (5):

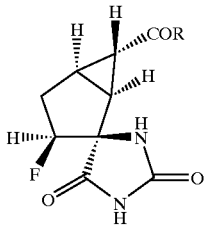

(5)

[in the formula, R is the same as described above], or an (1S, 2S, 3S, 5R, 6S)- or (1SR, 2SR, 3SR, 5RS, 6SR)-aminocyanide derivative represented by Formula (6):

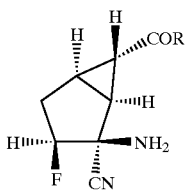

(6)

[in the formula, R is the same as described above]; and
subjecting them to a hydrolysis.

The terms used in the present invention are defined in the following. In the present invention, "$C_n$–$C_m$" means that the group following the "$C_n$–$C_m$" has from n to m carbon atoms.

The $C_1$–$C_6$ alkyl group means a straight-chain or branched-chain alkyl group having 1 to 6 carbon atoms, examples of which include a methyl group, an ethyl group, a propyl group, an isopropyl group, a butyl group, an isobutyl group, a t-butyl group, a pentyl group, an isopentyl group, a hexyl group, an isohexyl group, and the like.

The $C_3$–$C_6$ cycloalkyl group means a cyclic alkyl group having 3 to 6 carbon atoms, including, for example, a cyclopropyl group, a cyclopentyl group, a cyclohexyl group, or the like.

The ($C_3$–$C_6$ cycloalkyl) ($C_1$–$C_6$ alkyl) group means a group having a form mixed with a $C_3$–$C_6$ cycloalkyl group and a $C_1$–$C_6$ alkyl group, examples of which include a cyclopropylmethyl group, a cyclobutylmethyl group, a cyclopentylmethyl group, a cyclohexylmethyl group, and the like.

The aryl group means a phenyl group, a naphthyl group, or the like, and is preferably a phenyl group. The aryl ($C_1$–$C_6$ alkyl) means a straight-chain or branched-chain alkyl group having 1 to 6 carbon atoms, substituted with at least one aryl group, and preferably a phenyl group. Examples thereof include, for example, a benzyl group, a diphenylmethyl group, a 1-phenylethyl group, a 2-phenylethyl group, and the like.

The ($C_1$–$C_6$ alkoxy) ($C_1$–$C_6$ alkyl) group means a group having a form mixed with a $C_{1-6}$ alkoxy group and a $C_{1-6}$ alkyl group. The $C_1$–$C_6$ alkoxy group means a straight-chain or branched-chain alkoxy group having 1 to 6 carbon atoms, including, for example, a methoxy group, an ethoxy group, a propoxy group, an isopropoxy group, a butoxy group, an isobutoxy group, a t-butoxy group, a pentyloxy group, an isopentyloxy group, or the like. Therefore, examples of the ($C_1$–$C_6$ alkoxy) ($C_1$–$C_6$ alkyl) groups include a methoxyethyl group, an ethoxyethyl group, a propoxyethyl group, an isopropoxyethyl group, a butoxyethyl group, an isobutoxyethyl group, a pentyloxyethyl group, an isopentyloxyethyl group, and the like.

The $C_1$–$C_6$ hydroxyalkyl group means a $C_{1-6}$ alkyl group substituted with at least one hydroxyl group. Therefore, examples of the $C_1$–$C_6$ hydroxyalkyl group include a 2-hydroxyethyl group, a 3-hydroxypropyl group, a 2,3-dihydroxypropyl group, and the like.

The ($C_1$–$C_6$ alkylthio)($C_1$–$C_6$ alkyl) group means a group having a form mixed with a $C_1$–$C_6$ alkylthio group and a $C_1$–$C_6$ alkyl group. The $C_1$–$C_6$ alkylthio group means a straight-chain or branched-chain alkylthio group having 1 to 6 carbon atoms, including, for example, a methylthio group, an ethylthio group, a propylthio group, an isopropylthio group, a butylthio group, an isobutylthio group, a t-butylthio group, a pentylthio group, an isopentylthio group, and the like. Therefore, examples of the ($C_1$–$C_6$ alkylthio)($C_1$–$C_6$ alkyl) group include a methylthiomethyl group, a 2-methylthioethyl group, and the like.

The $C_1$–$C_6$ mercaptoalkyl group means a $C_1$–$C_6$ alkyl group substituted with at least one mercapto group. Therefore, examples of the $C_1$–$C_6$ mercaptoalkyl group include a 2-mercaptoethyl group, a 3-mercaptopropyl group, a 2,3-dimercaptopropyl group, and the like.

In each group described above, at least one hydrogen atom on the group may be substituted with an atom or a group, which is not hydrogen, for example, a halogen atom such as a fluorine atom, a chlorine atom, a bromine atom, or an iodine atom; a nitro group; an amino group; a hydroxyl group; a thiol group; a formyl group; a carboxyl group; a cyano group; a carbamoyl group; an alkyl group such as a methyl group, an ethyl group, a propyl group, an isopropyl group, a butyl group, an isobutyl group, a sec-butyl group, tert-butyl group, a pentyl group, an isopentyl group, a neopentyl group, or a tert-pentyl group; an aryl group and a heterocyclic group such as a phenyl group, a naphthyl group, a biphenyl group, an anthranyl group, a pyrrolyl group, a pyridyl group, or a thienyl group; an alkoxycarbonyl group such as a methoxycarbonyl group, or an ethoxycarbonyl group; an acyl group such as an acetyl group, or a benzoyl group; an alkoxy group such as a methoxy group, an ethoxy group, or a propoxy group; or an alkylthio group such as a methylthio group, an ethylthio group, or a propylthio group. Therefore, for example, a 2,2,2-trichloroethyl group, a phenacyl group, a 2,6-dimethylcyclohexyl group, and a 4-methoxybenzyl group and the like are included in a scope of $R^1$ and $R^2$. The number of the carbon atoms in these substituents is not included in the numbers n or m described above.

In addition, the pharmaceutically-acceptable salt in the present invention refers to, for example, a salt with an inorganic acid such as sulfuric acid, hydrogen chloride, or phosphoric acid; a salt with an organic acid such as acetic acid, oxalic acid, lactic acid, tartaric acid, fumaric acid, maleic acid, methanesulfonic acid, or benzenesulfonic acid; a salt with an amine such as trimethylamine, or methylamine; or a salt with a metal ion such as sodium ion, potassium ion, or calcium ion.

The compounds represented by Formulae (1) to (7) may be produced according to the synthetic methods described below (in the following reaction scheme, R represents the same substituent as described above).

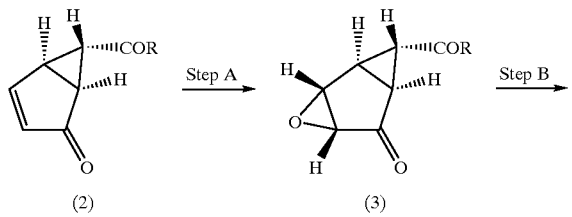

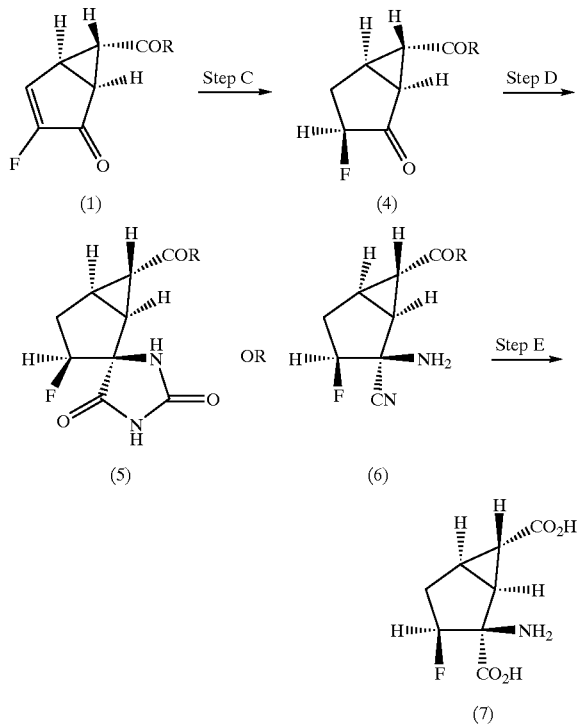

Step A: (1S, 5R, 6S)- or (1SR, 5RS, 6SR)-2-oxobicyclo[3.1.0]hex-3-ene-6-carboxylic acid derivative. (2) (in the following, referred to as "enone derivative (2)") is reacted with a peroxide in an inert solvent at a reaction temperature ranging from −30° C. to 150° C., and preferably from 0° C. to 50° C., to produce an epoxy derivative (3).

In this step, as examples of the inert solvent, mention may be made of, for example, alcohols such as methanol, ethanol, isopropyl alcohol, or ethylene glycol; ethers such as diethyl ether, tetrahydrofuran, dioxane, or 1,2-dimethoxyethane; hydrocarbons such as benzene or toluene; amides such as N,N-dimethylformamide; ketones such as acetone or ethyl methyl ketone; acetonitrile; water; acetic acid; trifluoroacetic acid; a mixture of these solvents; or the like. Examples of the peroxide include, for example, a peroxide of an organic carboxylic acid such as m-chloroperbenzoic acid or peracetic acid; a peroxide of an alcohol such as tert-butylhydroperoxide; hydrogen peroxide; and the like.

Step B: The epoxy derivative (3) is reacted with a fluorination agent in an inert solvent at a reaction temperature ranging from −30° C. to 200° C., and preferably from 0° C. to 150° C., to synthesize 3-fluoro-2-oxobicyclo[3.1.0]hex-3-ene-6-carboxylic acid derivative (1) which corresponds to the compound according to the present invention.

In this step, as examples of the inert solvent, mention maybe made of, for example, alcohols such as methanol, ethanol, isopropyl alcohol, or ethylene glycol; ethers such as diethyl ether, tetrahydrofuran, dioxane, or 1,2-dimethoxyethane; hydrocarbons such as benzene or toluene; amides such as N,N-dimethylformamide; or a mixture of these solvents. Examples of the fluorination agent include, for example, fluorine; hydrogen fluoride; an inorganic fluorinated compound such as potassium hydrogenfluoride ($HKF_2$); a quaternary ammonium fluorinated compound such as tetrabutylammonium fluoride; an N-fluoro-type fluorinated compound such as N-fluoropyridinium triflate, N-fluoro-N-t-butylbenzenesulfonamide, N-fluorosaccharinsultam, N-fluorobis(benzenesulfone) imide, N-fluoro-o-benzenesulfonimide; $ClO_3F$; $CF_3COOF$; and the like.

Step C: 3-Fluoro-2-oxobicyclo[3.1.0]hex-3-ene-6-carboxylic acid derivative (1) is hydrogenated in an inert solvent at a reaction temperature ranging from −30° C. to 100° C., and preferably from 0° C. to 50° C., to guide it to (1S, 3S, 5R, 6S)-or (1SR, 3SR, 5RS, 6SR)-3-fluoro-2-oxobicyclo[3.1.0]hexane-6-carboxylic acid derivative (4) (in the following, referred to as "fluoroketone derivative (4)").

In this step, as examples of the inert solvent, mention may be made of, for example, alcohols such as methanol, ethanol, isopropyl alcohol, or ethylene glycol; ethers such as diethyl ether, tetrahydrofuran, dioxane, or 1,2-dimethoxyethane; hydrocarbons such as benzene or toluene; amides such as N,N-dimethylformamide; water; or a mixture of these solvents. As the hydrogenation catalyst, a metal which is commonly employed as a hydrogenation catalyst, such as palladium/activated carbon, palladium black, platinum dioxide, or Raney Nickel may be employed. In the hydrogenation carried out in this step, hydrogen atoms are added stereoselectively to the double bond at the 3- and 4-position on the 5-membered ring, and for this reason, the fluorine atom in the fluoroketone derivative (4) may have the desired stereo-configuration.

Steps D and E: The fluoroketone derivative (4) is converted into a hydantoin derivative (5) or an aminocyanide derivative (6), or the like, according to the Strecker Amino Acid Synthesis (Ann., 75, 27 (1850); 91, 349 (1850)), the Bucherer-Bergs Reaction (J. Prakt. Chem., 140, 69 (1934)), or a modified method thereof, followed by hydrolysis, to produce (1S, 2S, 3S, 5R, 6S)- or (1SR, 2SR, 3SR, 5RS, 6SR)-2-amino-3-fluorobicyclo [3.1. 0]hexane-2,6-dicarboxylic acid (7) (in the following, referred to as "fluorine-containing amino acid derivative (7)")

Preferably, the fluoroketone derivative (4) is reacted with sodium cyanide or potassium cyanide and ammonium carbonate in a solvent of alcohols such as ethanol or a mixed solvent of water and an alcohol, preferably for 12 hours to 48 hours at 20° C. to 50° C., to derive the hydantoin derivative (5) which is a synthesis intermediate. Subsequently, the hydantoin derivative is subjected to hydrolysis by a base such as sodium hydroxide or an acid such as hydrochloric acid, hydrobromic acid, or sulfuric acid, in an inert solvent of, for example, alcohols such as ethanol, ethers such as dioxane, ketones such as acetone, water, or a mixture thereof, to synthesize a fluorine-containing amino acid derivative (7).

In the case where (1SR, 5RS, 6SR)-enone derivative (2) is employed as a starting material, the hydantoin derivative (5) or an aminocyanide derivative (6) synthesized by Steps A, B, C, and D may be optically resolved by the HPLC method employing chiral carriers such as cellulose carbamate derivatives or amylosecarbamate derivatives. In addition, the carboxylic acid derivatives derived by ester hydrolysis of the hydantoin derivative (5) or the aminocyanide derivative (6) synthesized according to Steps A, B, C, and D under the general basic conditions or acidic conditions, and the fluorine-containing amino acid derivative (7) may be optically resolved by the HPLC method employing chiral carriers such as cellulose carbamate derivatives or amylosecarbamate derivatives, or alternatively, may be optically resolved by using optically active amines such as (+)- or (−)-1-phenylethylamine, (+)- or (−)-phenylglycinol, (+)- or (−)-2-amino-1-butanol, (+)- or (−)-alaninol, brucine, cinchonidine, cinchonine, quinine, quinidine, or dehydroabiethylamine.

The fluorine-containing amino acid derivative (7) maybe converted into an ester derivative by protecting the amino group using an appropriate protecting group, subsequently, esterifying the amino-protected derivative using an alkyl halide or an alcohol, according to a common method, and subsequently, removing the protecting group of the amino group. The protection of the amino group, esterification, and deprotection of the amino group are carried out according to the common methods as described in PROTECTIVE GROUPS IN ORGANIC SYNTHESIS (written by THEODORA W. GREENE AND PETER G. M. WUTS), which is incorporated herein by reference. The ester derivative described above does not act on group 2 metabotropic glutamate receptor. However, this ester derivative is subjected to hydrolysis in vivo, converting to the corresponding carboxylic acid which acts on group 2 metabotropic glutamate receptors. As described above, the ester derivative functions as a prodrug, and for this reason, it is an extremely useful compound. The aminocyanide derivative (6), the fluorine-containing amino acid derivative (7), and the ester derivative of the fluorine-containing amino acid derivative (7) obtained by the methods described above may be optically resolved using optically active organic acids such as (+)- or (−)-di-p-toluoyl tartaric acid, (+)- or (−)-dibenzoyl tartaric acid, (+)- or (−)-tartaric acid, (+)- or (−)-mandelic acid, (+)- or (−)-camphoric acid, or (+)- or (−)-camphorsulfonic acid.

BEST MODES FOR CARRYING OUT THE INVENTION

In the following, the representative examples of the present invention are described. However, it should be understood that the present invention is not limited to these examples.

EXAMPLE 1

Syntheses of ethyl (1S, 3R, 4R, 5R, 6S)-, as well as ethyl and isopropyl (1SR, 3RS, 4RS, 5RS, 6SR)-3,4-epoxy-2-oxobicyclo[3.1.0] hexane-6-carboxylate In 4 ml of toluene, 0.60 g of ethyl (1SR, 5RS, 6SR)-2-oxobicyclo[3. .0]hex-3-ene-6-carboxylate were dissolved, and subsequently, 0.8 ml of a 70% aqueous solution of tert-butylhydroperoxide and 0.3 ml of a 10% methanol solution of benzyl trimethylammonium hydroxide were added thereto. The mixture was stirred for 20 minutes at room temperature. The reaction mixture was poured into water and extracted with ether. The organic layer was washed with a saturated aqueous solution of sodium chloride, and dried over anhydrous magnesium sulfate. The desiccant was filtered off, and the filtrate was concentratedunder reduced pressure. The residuewaspurified by a chromatography (silica gel: Wako gel C200 (produced by Wako Pure Chemical Industries Ltd.), eluent: hexane—ethyl acetate =6:1), yielding 0.58 g of ethyl (1SR, 3RS, 4RS, 5RS, 6SR)-3,4-epoxy-2-oxobicyclo[3.1.0]hexane-6-carboxylate.

The proton NMR and mass spectrograph data of ethyl (1SR, 3RS, 4RS, 5RS, 6SR)-3,4-epoxy-2-oxobicyclo[3.1.0] hexane-6-carboxylate are shown below.

$^1$H-NMR (CDCl$_3$) δ (ppm); 1.28 (3H, t, J 7.0 Hz), 2.09 (H, t, J=3.1 Hz), 2.21 (1H, ddt, J=5.3 Hz, 2.4 Hz, 1.1 Hz), 2.96 (1H, m), 3.25 (1H, dt, J=2.4 Hz, 1.1 Hz), 4.00 (1H, t, J=2.4 Hz), 4.17 (2H, q, J=7.0 Hz). MS (EI) m/e; 182 (M$^+$).

In the same manner as described above, from 2.80 g of isopropyl (1SR, 5RS, 6SR)-2-oxobicyclo[3.1.0]hex-3-ene- 6-carboxylate, 2.42 g of isopropyl (1SR, 3RS, 4RS, 5RS, 6SR)-3,4-epoxy-2-oxobicyclo[3.1.0]hexane-6-carboxylate was obtained.

The proton NMR and mass spectrograph data of isopropyl (1SR, 3RS, 4RS, 5RS, 6SR)-3,4-epoxy-2-oxobicyclo[3.1.0] hexane-6 -carboxylate are shown below.

$^1$H-NMR (CDCl$_3$) δ (ppm); 1.24 (3H, d, J=6.2 Hz), 1.25 (3H, d, J=6.2 Hz), 2.06 (1H, t, J=3.1 Hz), 2.19 (1H, m), 2.94 (1H, m), 3.23 (1H, m), 4.00 (1H, t, J=2.3 Hz), 5.01 (1H, sept, J=6.2 Hz). MS (EI) m/e; 196 (M$^+$).

In addition, in the same manner as described above, from 7.00 g of ethyl (1S, 5R, 6S)-2-oxobicyclo[3.1.0]hex-3-ene-6-carboxylate, 5.52 g of ethyl (1S, 3R, 4R, 5R, 6S)-3,4-epoxy-2-oxobicyclo[3.1.0]hexane-6-carboxylate was obtained.

The proton NMR, mass spectrograph, and specific rotation data of ethyl (1S, 3R, 4R, 5R, 6S)-3,4-epoxy-2-oxobicyclo [3.1. 0]hexane-6-carboxylate are shown below.

$^1$H-NMR (CDCl$_3$) δ (ppm); 1.28 (3H, t, J=7.0 Hz), 2.09 (1H, t, J=3. 1 Hz), 2.21 (1H, ddt, J=5.3 Hz, 2.4 Hz, 1.1 Hz), 2.96 (1H, m), 3.25 (1H, dt, J=2.4 Hz, 1.1 Hz), 4.00 (1H, t, J=2.4 Hz), 4.17 (2H, q, J 7.0 Hz). MS (EI) m/e; 182 (M$^+$). [α]$_D^{25}$=+12.23 (c=0.41, CH$_2$Cl$_2$).

EXAMPLE 2

Syntheses of (1SR, 3RS, 4RS, 5RS, 6SR)-N-methyl-3,4-epoxy-2-oxobicyclo [3.1.0] hexane-6-carboxyamide and (1SR, 3RS, 4SR, 5SR, 6SR)-N,N-dimethyl-3,4-epoxy-2-oxobicyclo[3.1.0]hexane-6-carboxyamide In the same manner as described in Example 1, from 1.50 g of (1SR, 5RS, 6SR)-N-methyl-2-oxobicyclo[3.1.0]-hex-3-ene-6-carboxyamide, 1.04 g of (1SR, 3RS, 4RS, 5RS, 6SR)-N-methyl-3,4-epoxy-2-oxobicyclo[3.1.0]hexane-6-carboxyamide was obtained.

$^1$H-NMR (CDCl$_3$) δ (ppm); 1.82 (1H, t, J=2.9 Hz), 2.18 (1H, ddt, J=5.2, 2.6, 1.1 Hz), 2.84 (3H, d, J=4.8 Hz), 2.97–3.02 (1H, m), 3.22 (1H, dt, J=2.4, 1.1 Hz), 3.97 (1H, t, J=2.4 Hz), 5.79 (1H, s). MS (ES) (Nega) m/e; 166 (M$^+$−1).

In the same manner as described above, from 2.71 g of (1SR, 5RS, 6SR)-N,N-dimethyl-2-oxobicyclo[3.1.0]hex-3-ene-6-carboxyamide, 1.88 g of (1SR, 3RS, 4RS, 5RS, 6SR)-N,N-dimethyl-3,4-epoxy-2-oxobicyclo[3.1.0]hexane-6-carboxyamide was obtained.

$^1$H-NMR (CDCl$_3$) δ (ppm); 2.12–2.16 (1H, m), 2.23 (1H, t, J=3.1 Hz), 2.96 (3H, s), 3.03–3.07 (1H, m), 3.14 (3H, s), 3.24–3.25 (1H, m), 3.99 (1H, t, J=2.3 Hz). MS (EI) (Pos) m/e; 181 (M$^+$)

EXAMPLE 3

Syntheses of ethyl and 2-hydroxyethyl (1S, 5R, 6S)-, as well as ethyl, isopropyl, and 2-hydroxyethyl (1SR, 5RS, 6SR)-3-fluoro-2-oxobicyclo[3.1.0]hex-3-ene-6-carboxylate Under a nitrogen atmosphere, 2.00 g of ethyl (1SR, 3RS, 4RS, 5RS, 6SR)-3,4-epoxy-2-oxobicyclo[3.1.0]hexane-6-carboxylate and 8.60 g of potassium hydrogen fluoride were suspended in 30 ml of ethylene glycol, and the suspension was stirred for 2 hours at 130° C. The reaction mixture was poured into water. The mixture was extracted with chloroform, and subsequently, dried over anhydrous magnesium sulfate. After the desiccant was filtered off, the filtrate was concentrated under reduced pressure. The residue was purified by a chromatography (silica gel: Wako gel C200 (produced by Wako Pure Chemical Industries Ltd.), eluent: hexane-ethyl acetate=4:1–1:2), yielding 0.49 g of ethyl (1SR, 5RS, 6SR)-3-fluoro-2-oxobicyclo[3.1.0]hex-3-ene-6-carboxylate and 0.84 g of 2-hydroxyethyl (1SR, 5RS, 6SR)-3-fluoro-2-oxobicyclo[3.1.0]hex-3-ene-6-carboxylate.

The proton NMR and mass spectrograph data of ethyl (1SR, 5RS, 6SR)-3-fluoro-2-oxobicyclo[3.1.0]hex-3-ene-6-carboxylate are shown below.

$^1$H-NMR (CDCl$_3$) δ (ppm); 1.28 (3H, t, J=7.0 Hz), 2.48 (1H, dt, J=3.1 Hz, J=0.7 Hz), 2.58 (1H, m), 2.81 (1H, m), 4.17 (2H, q, J=7.0 Hz), 6.91 (1H, m). MS (CI) m/e; 185 (M$^+$+1).

The proton NMR and mass spectrograph data of 2-hydroxyethyl (1SR, 5RS, 6SR)-3-fluoro-2-oxobicyclo [3.1.0]hex-3-ene-6-carboxylate are shown below.

$^1$H-NMR (CDCl$_3$) δ (ppm); 1.72–1.92 (1H, brs), 2.54 (1H, t, J=3.0 Hz), 2.61 (1H, m), 2.84 (1H, m), 3.80–3.92 (2H, m), 4.23–4.30 (2H, m), 6.92 (1H, m). MS (CI) m/e; 201 (M$^+$+1).

In the same manner as described above, from 2.85 g of isopropyl (1SR, 3RS, 4RS, 5RS, 6SR)-3,4-epoxy-2-oxobicyclo[3.1.0]hexane-6-carboxylate, 1.01 g of isopropyl (1SR, 5RS, 6SR)-3-fluoro-2-oxobicyclo[3.1.0]hex-3-ene-6-carbo xylate, and 0.49 g of 2-hydroxyethyl (1SR, 5RS, 6SR)-3-fluoro-2-oxobicyclo[3.1.0]hex-3-ene-6-carboxylate were obtained.

The proton NMR and mass spectrograph data of isopropyl (1SR, 5RS, 6SR)-3-fluoro-2-oxobicyclo[3.1.0]hex-3-ene-6-carbo xylate are shown below.

$^1$H-NMR (CDCl$_3$) δ (ppm); 1.24 (3H, d, J=6.2 Hz), 1.25 (3H, d, J=6.2 Hz), 2.45 (1H, t, J=2.8 Hz), 2.57 (1H, m), 2.79 (1H, m), 5.00 (1H, sept, J=6.2 Hz), 6.90 (1H, m). MS (CI) m/e; 199 (M$^+$+1).

In addition, in the same manner as described above, from 5.45 g of ethyl (1S, 3R, 4R, 5R, 6S)-3,4-epoxy-2-oxobicyclo [3.1.0]hexane-6-carboxylate, 1.01 g of ethyl (1S, 5R, 6S)-3-fluoro-2-oxobicyclo[3.1.0]hex-3-ene-6-carboxyl ate, and 1.67 g of 2-hydroxyethyl (1S, 5R, 6S)-3-fluoro-2-oxobicyclo[3.1.0]hex-3-ene-6-carboxylate were obtained.

The proton NMR, mass spectrograph, and specific rotation data of ethyl (1S, 5R, 6S)-3-fluoro-2-oxobicyclo[3.1.0] hex-3-ene-6-carboxylate are shown below.

$^1$H-NMR (CDCl$_3$) δ (ppm); 1.28 (3H, t, J=7.0 Hz), 2.48 (1H, dt, J=3.1 Hz, J=0.7 Hz), 2.58 (1H, m), 2.81 (1H, m), 4.17 (2H, q, J=7.0 Hz), 6.91 (1H, m). MS (CI) m/e; 185 (M$^+$+1). [α]$_D^{25}$=−96.75 (c=0.43, CH$_2$Cl$_2$)

The proton NMR, mass spectrograph, and specific rotation data of 2-hydroxyethyl (1S, 5R, 6S)-3-fluoro-2-oxobicyclo [3.1.0]hex-3-ene-6-carboxylate are shown below.

$^1$H-NMR (CDCl$_3$) δ (ppm); 1.72–1.92 (1H, brs), 2.54 (1H, t, J=3.0 Hz), 2.61 (1H, m), 2.84 (1H, m), 3.80–3.92 (2H, m), 4.23–4.30 (2H, m), 6.92 (1H, m). MS (CI) m/e; 201 (M$^+$+1). [α]$_D^{25}$=−181.30 (c=0.41, CH$_2$Cl$_2$)

EXAMPLE 4

Syntheses of (1SR, 5RS, 6SR)-N-methyl-3-fluoro-2-oxobicyclo[3.1.0]hex-3-ene-6-carboxyamide and (1SR, 5RS, 6SR)-N,N-dimethyl-3-fluoro-2-oxobicyclo[3.1.0]-hex-3-ene-6-carboxyamide In the same manner as described in Example 3, from 0.98 g of (1SR, 3RS, 4RS, 5RS, 6SR)-N-methyl-3,4-epoxy-2-oxobicyclo[3.1.0]hexane-6-carboxyamide, 0.57 g of (1SR, 5RS, 6SR)-N-methyl-3-fluoro-2-oxobicyclo[3.1.0] hex-3-ene-6-carboxyamide was obtained.

$^1$H-NMR (CDCl$_3$) δ (ppm); 2.24 (1H, t, J=2.8 Hz), 2.56–2.62 (1H, m), 2.83 (3H, d, J=5.0 Hz), 2.80–2.89 (1H, m), 5.84 (1H, s), 6.89 (1H, dt, J=2.8, 1.3 Hz). MS (ES) (Nega) m/e; 168 (M$^+$−1).

In the same manner as described above, from 1.68 g of (1SR, 3RS, 4RS, 5RS, 6SR)-N,N-dimethyl-3,4-epoxy-2-oxobicyclo[3.1.0]hexane-6-carboxyamide, 0.84 g of (1SR, 5RS, 6SR)-N,N-dimethyl-3-fluoro-2-oxobicyclo[3.1.0]hex-3-ene-6-carboxyamide were obtained.

$^1$H-NMR (CDCl$_3$) δ (ppm); 2.56–2.63 (2H, m), 2.87–2.94 (1H, m), 2.95 (3H, s), 3.14 (3H, s), 6.91 (1H, dt, J=2.8, 1.3 Hz). MS (ES) (Nega) m/e; 182 (M$^+$–1)

EXAMPLE 5

Syntheses of ethyl and 2-hydroxyethyl (1S, 3S, 5R, 6S)-, as well as ethyl, isopropyl, and 2-hydroxyethyl (1SR, 3SR, 5RS, 6SR)-3-fluoro-2-oxobicyclo[3.1.0]hexane-6-carboxylate In 4.8 ml of ethanol, 0.47 g of ethyl (1SR, 5RS, 6SR)-3-fluoro-2-oxobicyclo[3.1.0]hex-3-ene-6-carboxylate were dissolved. 48mg of 5%-palladium/activated carbon was added thereto, and subsequently, stirred overnight at room temperature under a hydrogen atmosphere. The reaction mixture was filtered using celite. The filtrate was concentrated under reduced pressure. The residue was purified by a chromatography (silica gel: Wako gel C200 (produced by Wako Pure Chemical Industries Ltd.), eluent: hexane-ethyl acetate=4:1), yielding 0.36 g of ethyl (1SR, 3SR, 5RS, 6SR)-3-fluoro-2-oxobicyclo[3.1.0]hexane-6-carboxylate.

The proton NMR and mass spectrograph data of ethyl (1SR, 3SR, 5RS, 6SR)-3-fluoro-2-oxobicyclo[3.1.0]hexane-6-carboxylate are shown below.

$^1$H-NMR (CDCl$_3$) δ (ppm); 1.29 (3H, t, J=7.2 Hz), 2.00–2.70 (5H, m), 4.18 (2H, q, J=7.2 Hz), 4.51 (1H, dd, J=51.0 Hz, J=8.1 Hz). MS (Ion Spray) (Nega) m/e; 185 (M$^+$–1).

In the same manner as described above, from 0.83 g of 2-hydroxyethyl (1SR, 5RS, 6SR)-3-fluoro-2-oxobicyclo[3.1.0]hex-3-ene-6-carboxylate, 0.67 g of 2-hydroxyethyl (1SR, 3SR, 5RS, 6SR)-3-fluoro-2-oxobicyclo[3.1.0]hexane-6-carboxylate was obtained, and from 0.66 g of isopropyl (1SR, 5RS, 6SR)-3-fluoro-2-oxobicyclo [3.1. 0]hex-3-ene-6-carboxylate, 0.39 g of isopropyl (1SR, 3SR, 5RS, 6SR)-3-fluoro-2-oxobicyclo[3.1.0]hexane-6-carboxylate was obtained.

The proton NMR and mass spectrograph data of 2-hydroxyethyl (1SR, 3SR, 5RS, 6SR)-3-fluoro-2-oxobicyclo[3.1.0]hexane-6-carboxylate are shown below.

$^1$H-NMR (CDCl$_3$) δ (ppm); 1.92–2.90 (6H, m), 3.66–4.04 (2H, m), 4.20–4.50 (2H, m), 4.55 (1H, dd, J=51.2 Hz, J=7.5 Hz). MS (Ion Spray) (Nega) m/e; 201 (M$^+$–1).

The proton NMR and mass spectrograph data of isopropyl (1SR, 3SR, 5RS, 6SR)-3-fluoro-2-oxobicyclo[3.1.0]hexane-6-carboxylate are shown below.

$^1$H-NMR (CDCl$_3$) δ (ppm); 1.25 (3H, d, J=6.2 Hz), 1.26 (3H, d, J=6.2 Hz), 1.96–2.64 (5H, m), 4.52 (1H, dd, J=50.4 Hz, J=7.6 Hz), 5.02 (1H, sept, J=6.2 Hz). MS (EI) m/e; 200 (M$^+$).

In addition, in the same manner as described above, from 0.80 g of ethyl (1S, 5R, 6S)-3-fluoro-2-oxobicyclo[3.1.0]hex-3-ene-6-carboxylate, 0.61 g of ethyl (1S, 3S, 5R, 6S)-3-fluoro-2-oxobicyclo [3.1.0]hexane-6-carboxylate was obtained, and from 1.31 g of 2-hydroxyethyl (1S, 5R, 6S)-3-fluoro-2-oxobicyclo[3.1.0]hex-3-ene-6-carboxylate, 0.83 g of 2-hydroxyethyl (1S, 3S, 5R, 6S)-3-fluoro-2-oxobicyclo[3.1.0]hexane-6-carboxylate was obtained.

The proton NMR, mass spectrograph, and specific rotation data of ethyl (1S, 3S, 5R, 6S)-3-fluoro-2-oxobicyclo [3.1.0]hexane-6-carboxylate are shown below.

$^1$H-NMR (CDCl$_3$) δ (ppm); 1.29 (3H, t, J=7.2 Hz), 2.00–2.70 (5H, m), 4.18 (2H, q, J=7.2 Hz), 4.51 (1H, dd, J=51.0 Hz, J=8.1 Hz). MS (Ion Spray) (Nega) m/e; 185 (M$^+$–1). [α]$_D^{22}$=–11.70 (c=0.45, CH$_2$Cl$_2$).

The proton NMR, mass spectrograph, and specific rotation data of 2-hydroxyethyl (1S, 3S, 5R, 6S) 3-fluoro-2-oxobicyclo[3.1.0]hexane-6-carboxylate are shown below.

$^1$H-NMR (CDCl$_3$) δ (ppm); 1.92–2.90 (6H, m), 3.66–4.04 (2H, m), 4.20–4.50 (2H, m), 4.55 (1H, dd, J=51.2 Hz, J=7.5 Hz). MS (Ion Spray) (Nega) m/e; 201 (M$^+$–1). [α]$_D^{25}$=–9.98 (c=0.50, CH$_2$Cl$_2$).

EXAMPLE 6

Syntheses of ethyl (1S, 2S, 3S, 5R, 6S)- and (1SR, 2SR, 3SR, 5RS, 6SR)-2-spiro-5'-hydantoin-3-fluorobicyclo[3.1.0]hexane-6-carboxylate In a mixed solution of 1.7 ml of water and 2.6ml of ethanol, 0.33 g of ethyl (1SR, 3SR, 5RS, 6SR)-3-fluoro-2-oxobicyclo[3.1.0]hexane-6-carboxylate was dissolved. Ammonium carbonate in an amount of 0.42 g and potassium cyanide in an amount of 0.13 g were added thereto, and subsequently, the mixture was stirred for 3 days at 35° C. After the reaction solution was concentrated under reduced pressure, a saturated aqueous solution of sodium chloride was added to the residue. The mixture was extracted with ethyl acetate and chloroform, and subsequently, dried over anhydrous magnesium sulfate. After the desiccant was filtered off, the filtrate was concentrated under reduced pressure. The residue was recrystallized from water-ethanol=1:1, and subsequently, purified by a chromatography (silica gel: Wako gel C200 (produced by Wako Pure Chemical Industries Ltd.), eluent: chloroform-methanol=30:1), yielding 0.23 g of ethyl (1SR, 2SR, 3SR, 5RS, 6SR)-2-spiro-5'-hydantoin-3-fluorobicyclo[3.1.0]hexane-6-carboxylate.

The proton NMR and mass spectrograph data of ethyl (1SR, 2SR, 3SR, 5RS, 6SR)-2-spiro-5'-hydantoin-3-fluorobicyclo[3.1.0]hexane-6-carboxylate are shown below.

$^1$H-NMR (DMSO-d$_6$) δ (ppm); 1.19 (3H, t, J=7.0 Hz), 1.95–2.46 (5H, m), 4.06 (2H, q, J=7.0 Hz), 4.81 (1H, dd, J=52.4 Hz, 5.1 Hz), 8.44 (1H, s), 10.91 (1H, s). MS (EI) m/e; 256 (M$^+$)

In addition, in the same manner as described above, from 0.28 g of ethyl (1S, 3S, 5R, 6S)-3-fluoro-2-oxobicyclo [3.1.0]hexane-6-carboxylate, 0.23 g of ethyl (1S, 2S, 3S, 5R, 6S)-2-spiro-5'-hydantoin-3-fluorobicyclo[3.1.0]hexane-6-carboxylate was obtained.

The proton NMR, mass spectrograph, and specific rotation data of ethyl (1S, 2S, 3S, 5R, 6S)-2-spiro-5'-hydantoin-3-fluorobicyclo[3.1.0]hexane-6-carboxylate are shown below.

$^1$H-NMR (DMSO-d$_6$) δ (ppm); 1.19 (3H, t, J=7.0 Hz), 1.95–2.46 (5H, m), 4.06 (2H, q, J=7.0 Hz), 4.81 (1H, dd, J=52.4 Hz, 5.1 Hz), 8.44 (1H, s), 10.91 (1H, s). MS (EI) m/e; 256 (M$^+$). [α]$_D^{25}$=+30.11 (c=0.12, MeOH).

EXAMPLE 7

Syntheses of ethyl (1S, 2S, 3S, 5R, 6S)- and (1SR, 2SR, 3SR, 5RS, 6SR)-2-amino-3-fluorobicyclo [3.1.0]hexane-2,6-dicarboxylic acid In 1.5 ml of 60% sulfuric acid, 100 mg of ethyl (1SR, 2SR, 3SR, 5RS, 6SR)-2-spiro-5'-hydantoin-3-fluorobicyclo [3.1. 0]hexane-6-carboxylate was dissolved. The mixture was heated for 12 hours at 140° C. After the reaction solution was allowed to cool to room temperature, a 5M aqueous solution of sodium hydroxide was added thereto so that the reaction mixture had pH8. Purification was carried out using an ion exchange chromatography (AG1-X8 anion exchange resin (Bio-Rad), eluent: 0. 1M acetic acid-2M acetic acid), yielding 20 mg of (1SR, 2SR, 3SR, 5RS, 6SR)-2-amino-3-fluorobicyclo[3.1.0]hexane-2,6-dicarboxylic acid.

The proton NMR and mass spectrograph data of (1SR, 2SR, 3SR, 5RS, 6SR)-2-amino-3-fluorobicyclo[3.1.0]hexane-2,6-dicarboxylic acid are shown below.

$^1$H-NMR (TFA-d) δ (ppm); 2.49 (1H, brs), 2.59–3.06 (4H, m), 5.40 (1H, dd, J=52.1 Hz, 5.3 Hz). MS (CI) m/e; 204 (M$^+$+1).

In the same manner as described above, from 0.12 g of ethyl (1S, 2S, 3S, 5R, 6S)-2-spiro-5'-hydantoin-3-fluorobicyclo[3.1.0]hexane-6-carboxylate, 75 mg of (1S, 2S, 3S, 5R, 6S)-2-amino-3-fluorobicyclo[3.1.0]hexane-2,6-dicarboxylic acid was obtained.

The proton NMR, mass spectrograph, and specific rotation data of (1S, 2S, 3S, 5R, 6S)-2-amino-3-fluorobicyclo[3.1.0]hexane-2,6-dicarboxylic acid are shown below.

$^1$H-NMR (TFA-d) δ (ppm); 2.49 (1H, brs), 2.59–3.06 (4H, m), 5.40 (1H, dd, J=52.1 Hz, 5.3 Hz). MS (CI) m/e; 204 (M$^+$+1) [α]$_D^{25}$=+58.61 (c=0.20, 1N HCl).

EXAMPLE 8

Synthesis of (1S, 2S, 3S, 5R, 6S)-2-amino-3-fluorobicyclo [3.1. 0]hexane-2,6-dicarboxylic acid (1) A mixture of 2.20 g of ethyl (1SR, 2SR, 3SR, 5RS, 6SR)-2-spiro-5'-hydantoin-3-fluorbicyclo[3.1.0]hexane-6-carboxylate and 17 ml of 2N sodium hydroxide was stirred at room temperature. After the mixture was stirred for 2 hours, concentrated hydrochloric acid was added thereto to adjust the pH of the mixture to 1.0. The generated crystals were isolated by means of filtration, and subsequently, dried, yielding 1.81 g of (1SR, 2SR, 3SR, 5RS, 6SR)-2-spiro-5'-hydantoin-3-fluorobicyclo[3.1.0]hexane-6-carboxylic acid.

The proton NMR and mass spectrograph data of (1SR, 2SR, 3SR, 5RS, 6SR)-2-spiro-5'-hydantoin-3-fluorobicyclo[3.1.0]hexane-6-carboxylic acid are shown below.

$^1$H-NMR (DMSO-d$_6$) δ (ppm); 1. 85–2.44 (5H, m), 4.80 (1H, dd, J=52.3 Hz, 5.3 Hz), 8.44 (1H, s), 10.88 (1H, s), 12.30 (1H, brs). MS (FAB) (Nega) m/e; 227 (M$^+$–1).

(2) In 26 ml of a mixed solution of acetone : water=8:5, 1.80 g of (1SR, 2SR, 3SR, 5RS, 6SR)-2-spiro-5'-hydantoin-3-fluorobicyclo[3.1.0]hexane-6-carboxylic acid was stirred at 55° C. After 0.96 g of (R)-(+)-1-phenylethylamine was added thereto, the mixture was stirred for 15 hours at room temperature. The generated crystals were filtered to obtain 1.30 g of (R)-(+)-1-phenylethylamine salt. In 15 ml of water, 1.20 g of said salt was suspended, and subsequently, the pH of the suspension was adjusted to 1.0 using 1M hydrochloric acid. The suspension was stirred for 14 hours at room temperature. The generated crystals were isolated by means of filtration, obtaining 0.65 g of (1S, 2S, 3S, 5R, 6S)-2-spiro-5'-hydantoin-3-fluorobicyclo[3.1.0]hexane-6-carboxylic acid. In addition, the filtrate was purified by an ion exchange chromatography (AG50W-X8 cation exchange resin (Bio-Rad), eluent: 1M acetic acid), yielding 0.06 g of (1S, 2S, 3S, 5R, 6S)-2-spiro-5'-hydantoin-3-fluorobicyclo[3.1.0]hexane-6-carboxylic acid.

The proton NMR, mass spectrograph, and specific rotation data of (1S, 2S, 3S, 5R, 6S)-2-spiro-5'-hydantoin-3-fluorobicyclo[3.1.0]hexane-6-carboxylic acid are shown below.

$^1$H-NMR (DMSO-d$_6$) δ (ppm); 1.85–2.44 (5H, m), 4.80 (1H, dd, J=52.3 Hz, 5.3 Hz), 8.44 (1H, s), 10.88 (1H, s), 12.30 (1H, brs). MS (FAB) (Nega) m/e; 227 (M$^+$–1). [α]$_D^{22}$=+36.84 (c=0.20, MeOH).

(3) In 246 ml of 60% sulfuric acid, 14.78 g of (1S, 2S, 3S, 5R, 6S)-2-spiro-5'-hydantoin-3-fluorobicyclo[3.1.0]hexane-6-carboxylic acid was dissolved. The solution was stirred for 2 days at 140° C. After the reaction solution was allowed to cool to room temperature, and subsequently, the pH thereof was adjusted to pH8 using a 5M aqueous solution of sodium hydroxide, it was purified by an ion exchange chromatography (AG1-X8 anion exchange resin (Bio-Rad), eluent: 0.1M acetic acid-2M acetic acid), yielding 7.65 g of (1S, 2S, 3S, 5R, 6S)-2-amino-3-fluorobicyclo[3.1.0]hexane-2,6-dicarboxylic acid. The specific rotation data thereof is shown below. [α]$_D^{22}$=+58.61 (c=0.20, 1N HCl).

INDUSTRIAL APPLICABILITY

The compounds according to the present invention, (1S, 5R, 6S)- or (1SR, 5RS, 6SR)-3-fluoro-2-oxobicyclo [3.1.0]hex-3-ene-6-carboxylic acid derivatives are useful as intermediates for synthesis of a fluorine-containing amino acid derivative ((1S, 2S, 3S, 5R, 6S)- or (1SR, 2SR, 3SR, 5RS, 6SR)-2-amino-3-fluorobicyclo[3.1.0]hexane-2,6-dicarboxylic acid) acting on group 2 metabotropic glutamate receptors, which has treatment effects or prevention effects on psychiatric disorders such as, for example, schizophrenia, anxiety and its associated diseases, depression, bipolar disorder, and epilepsy; and neurological diseases such as drug dependence, cognitive disorders, Alzheimer's disease, Huntington's chorea, Parkinson's disease, dyskinesia associated with muscular stiffness, cerebral ischemia, cerebral failure, myelopathy, and head trauma.

In addition, according to the process for producing the fluorine-containing amino acid derivative of the present invention, employing (1S, 5R, 6S)- or (1SR, 5RS, 6SR)-3-fluoro-2-oxobicyclo[3.1.0]hex-3-ene-6-carboxylic acid derivative, as a starting material, in the initial step of the process, a fluorine atom can be inserted stereoselectively, and for this reason, the desired fluorine-containing amino acid derivative described above can be produced efficiently.

What is claimed is:

1. A (1S, 5R, 6)- or (1SR, 5RS, 6SR)-3-fluoro-2-oxobicyclo [3.1.0] hex-3-ene-6-carboxylic acid derivative represented by Formula (1):

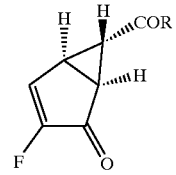

(1)

[in the formula, R represents OR$^1$ or NR$^1$R$^2$, wherein R$^1$ and R$^2$ are identical or different, and each represents a hydrogen atom, a C$_1$–C$_6$ alkyl group, a C$_3$–C$_6$ cycloalkyl group, a (C$_3$–C$_6$ cycloalkyl) (C$_1$–C$_6$ alkyl) group, an aryl group, an aryl (C$_1$–C$_6$ alkyl) group, a (C$_1$–C$_6$ alkoxy) (C$_1$–C$_6$ alkyl) group, a C$_{1-6}$ hydroxyalkyl group, a (C$_1$–C$_6$ alkylthio) (C$_1$–C$_6$ alkyl) group, or a C$_1$–C$_6$ mercaptoalkyl group].

2. The derivative according to claim 1, characterized in that in the case where R$^1$ and/or R$^2$ represent groups other than a hydrogen atom, at least one hydrogen atom on said groups is substituted with a group selected from the group consisting of a halogen atom, an alkyl group, an alkoxy group, an alkylthio group, a nitro group, an amino group, a hydroxyl group, a thiol group, a formyl group, a carboxyl group, an acyl group, an alkoxycarbonyl group, a cyano group, a carbamoyl group, an aryl group, and a heterocyclic group.

3. A process for producing a carboxylic acid derivative as recited in claim 1, characterized in that the process comprises the steps of:

oxidizing an (1S, 5R, 6S)- or (1SR, 5RS, 6SR)-2-oxobicyclo[3.1.0]hex-3-ene-6-carboxylic acid derivative represented by Formula (2):

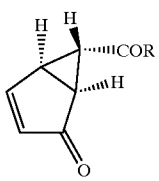

(2)

[in the formula, R represents $OR^1$ or $NR^1R^2$, wherein $R^1$ and $R^2$ are identical or different, and each represents a hydrogen atom, a $C_1$–$C_6$ alkyl group, a $C_3$–$C_6$ cycloalkyl group, a ($C_3$–$C_6$ cycloalkyl) ($C_1$–$C_6$ alkyl) group, an aryl group, an aryl ($C_1$–$C_6$ alkyl) group, a ($C_1$–$C_6$ alkoxy) ($C_1$–$C_6$ alkyl) group, a $C_1$–$C_6$ hydroxyalkyl group, a ($C_1$–$C_6$ alkylthio) ($C_1$–$C_6$ alkyl) group, or a $C_1$–$C_6$ mercaptoalkyl group] by means of a peroxide, to produce an (1S, 3R, 4R, 5R, 6S)- or (1SR, 3RS, 4RS, 5RS, 6SR)-epoxy derivative represented by Formula (3):

(3)

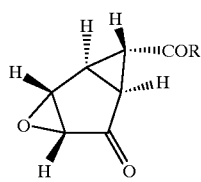

[in the formula, R is the same as described above]; and reacting said epoxy derivative with a fluorination agent.

4. The process according to claim 3, characterized in that in the case where $R^1$ and/or $R^2$ of the derivative of Formula (2) represent groups other than a hydrogen atom, at least one hydrogen atom on said groups is substituted with a group selected from the group consisting of a halogen atom, an alkyl group, an alkoxy group, an alkylthio group, a nitro group, an amino group, a hydroxyl group, a thiol group, a formyl group, a carboxyl group, an acyl group, an alkoxycarbonyl group, a cyano group, a carbamoyl group, an aryl group, and a heterocyclic group.

5. A process for producing an (1S, 2S, 3S, 5R, 6S)- or (1SR, 2SR, 3SR, 5RS, 6SR)-2-amino-3-fluorobicyclo[3.1.0]hexane-2,6-dicarboxylic acid represented by Formula (7):

(7)

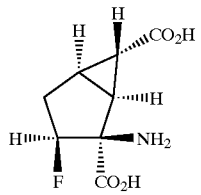

a pharmaceutically acceptable salt thereof, or a hydrate thereof, characterized in that the process comprises the steps of:

hydrogenating an (1S, 5R, 6S)- or (1SR, 5RS, 6SR)-3-fluoro-2-oxobicyclo[3.1.0]hex-3-ene-6-carboxylic acid derivative represented by Formula (1):

(1)

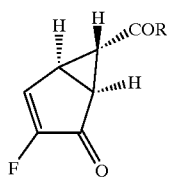

[in the formula, R represents $OR^1$ or $NR^1R^2$, wherein $R^1$ and $R^2$ are identical or different and each represents a hydrogen atom, a $C_1$–$C_6$ alkyl group, a $C_3$–$C_6$ cycloalkyl group, a ($C_3$–$C_6$ cycloalkyl) ($C_1$–$C_6$ alkyl) group, an aryl group, an aryl ($C_1$–$C_6$ alkyl) group, a ($C_1$–$C_6$ alkoxy) ($C_1$–$C_6$ alkyl) group, a $C_1$–$C_6$ hydroxyalkyl group, a ($C_1$–$C_6$ alkylthio) ($C_1$–$C_6$ alkyl) group, or a $C_1$–$C_6$ mercaptoalkyl group] to produce an (1S, 3S, 5R, 6S)- or (1SR, 3SR, 5RS, 6SR)-3-fluoro-2-oxobicyclo[3.1.0]hexane-6-carboxylic acid derivative represented by Formula (4):

(4)

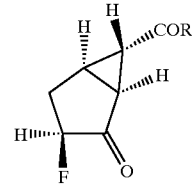

[in the formula, R is the same as described above];

subjecting said carboxylic acid derivative to hydantoination or aminocyanidation to produce an (1S, 2S, 3S, 5R, 6S)- or (1SR, 2SR, 3SR, 5RS, 6SR)-hydantoin derivative represented by Formula (5):

(5)

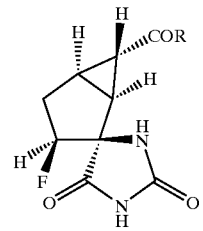

[in the formula, R is the same as described above], or an (1S, 2S, 3S, 5R, 6S)- or (1SR, 2SR, 3SR, 5RS, 6SR)-aminocyanide derivative represented by Formula (6):

(6)

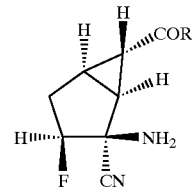

[in the formula, R is the same as described above]; and subjecting said hydantoin derivative or aminocyanide derivative to hydrolysis.

6. The process according to claim 5, characterized in that in the case where $R^1$ and/or $R^2$ of the derivative of Formula (1) represent groups other than a hydrogen atom, at least one hydrogen atom on said groups is substituted with a group selected from the group consisting of a halogen atom, an alkyl group, an alkoxy group, an alkylthio group, a nitro group, an amino group, a hydroxyl group, a thiol group, a formyl group, a carboxyl group, an acyl group, an alkoxycarbonyl group, a cyano group, a carbamoyl group, an aryl group, and a heterocyclic group.

* * * * *

UNITED STATES PATENT AND TRADEMARK OFFICE
CERTIFICATE OF CORRECTION

PATENT NO. : 6,392,086 B1
DATED : May 21, 2002
INVENTOR(S) : Nakazato et al.

It is certified that error appears in the above-identified patent and that said Letters Patent is hereby corrected as shown below:

Title page, Item [54] and Column 1, line 3,
Title, delete "BY".

Title page,
Item [56], FOREIGN PATENT DOCUMENTS, delete "WO 99/28839    1/1999"
Item [57], ABSTRACT,
Line 1, delete "inventions" and insert -- invention --.

Column 8,
Line 44, "[3. .0]" should read -- [3.1.0] --;
Line 54, "edunder" should read -- ed under --;
Line 54, "residuewaspurified" should read -- residue was purified --;
Line 62, "J 7.0 Hz" should read -- J=7.0 -- and
Line 63, "(H," should read -- (1H --.

Column 9,
Line 29, "5SR" should read -- 5RS --.

Column 10,
Line 28, "carbo xylate" should read -- carboxylate --;
Line 36, "carbo xylate" should read -- carboxylate --; and
Line 47, "oxobicyclo [3.1.0]" should read -- oxobicyclo[3.1.0] --.

Column 12,
Line 14, "and2.6ml" should read -- and 2.6 ml --.

Column 14,
Line 12, "for'" should read -- for --; and
Line 55, "atom ," should read -- atom, --.

UNITED STATES PATENT AND TRADEMARK OFFICE
CERTIFICATE OF CORRECTION

PATENT NO.   : 6,392,086 B1
DATED        : May 21, 2002
INVENTOR(S)  : Nakazato et al.

It is certified that error appears in the above-identified patent and that said Letters Patent is hereby corrected as shown below:

<u>Column 15,</u>
Line 17, "group]by" should read -- group [by --; and
Line 55, "carbo xylic" should read -- carboxylic --.

Signed and Sealed this

Twenty-sixth Day of November, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,392,086 B1 | Page 1 of 1 |
| APPLICATION NO. | : 09/857631 | |
| DATED | : May 21, 2002 | |
| INVENTOR(S) | : Nakazato et al. | |

It is certified that error appears in the above-identified patent and that said Letters Patent is hereby corrected as shown below:

On the title of the Patent, Under heading "(75) Inventors:", "Hisanako Ito" should read --Hisanaka Ito--.

Signed and Sealed this

Eighteenth Day of September, 2007

JON W. DUDAS
*Director of the United States Patent and Trademark Office*